United States Patent [19]

Wolf et al.

[11] Patent Number: 4,632,741

[45] Date of Patent: Dec. 30, 1986

[54] SYNTHESIS OF ALKYL PHOSPHINATE SALTS AND BIS(ALKYL) PHOSPHINATE SALTS

[75] Inventors: Stephen F. Wolf, St. Paul; Chung-Tsing Liu, Bloomington, both of Minn.

[73] Assignee: Economics Laboratory, Inc., St. Paul, Minn.

[21] Appl. No.: 838,097

[22] Filed: Mar. 10, 1986

Related U.S. Application Data

[63] Continuation-in-part of Ser. No. 647,918, Sep. 6, 1984, Pat. No. 4,590,014.

[51] Int. Cl.[4] ............................................. B01J 19/12
[52] U.S. Cl. ................................................ 204/157.73
[58] Field of Search ..................................... 204/157.73

[56] References Cited

U.S. PATENT DOCUMENTS 2,724,718  11/1955  Stiles et al. ..................... 204/157.73

Primary Examiner—Howard S. Williams
Attorney, Agent, or Firm—Merchant, Gould, Smith, Edell, Welter & Schmidt

[57] ABSTRACT

An improved method for the preparation of phosphinate salts or bis(alkyl) phosphinate salts by the reaction of an olefinic material with a hypophosphite salt by means of irradiation with UV light in the presence of a photoinitiator is disclosed.

9 Claims, No Drawings

SYNTHESIS OF ALKYL PHOSPHINATE SALTS AND BIS(ALKYL) PHOSPHINATE SALTS

CROSS-REFERENCE TO RELATED APPLICATIONS

This application is a continuation-in-part of application Ser. No. 647,918, filed Sept. 6, 1984, now U.S. Pat. No. 4,590,014.

BACKGROUND OF THE INVENTION

Alkyl phosphinates or bis(alkyl)phosphinates can be prepared by the reaction of an olefin with an alkali metal salt of hypophosphorous acid. For example, the reaction of a 1:1 mole ratio of an alpha-olefin with sodium hypophosphite yields the corresponding sodium alkyl phosphinate when initiated photochemically in the presence of a photoinitiator, or thermally in the presence of an introduced chemical source of free radicals such as a peroxide. The reaction may be summarized as follows:

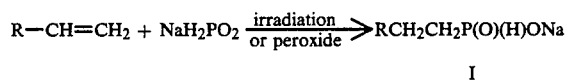

I

Alkyl phosphinate I can be converted into the corresponding phosphonate $(RCH_2CH_2P(O)(ONa)_2)$ by exposure to an oxidizing agent. Both the alkyl phosphonates and alkyl phosphinates can function as anionic surfactants, and can act to enhance the wetting power of aqueous media.

Although the alkali metal phosphinates may be useful as surfactants additives for household and industrial detergents, this potential has not been realized due to the barriers encountered to efficient, commercially-viable syntheses of this class of compounds. For example, numerous yield-reducing side reactions, including telomerization, double bond polymerization, abstraction of alkylic hydrogen atoms and hypophosphorous acid oxidation can occur. In *Tenside Detergents*, Vol. 18, 190 (1981), C. H. Agustin extensively examined reaction variables with respect to the synthesis of sodium octylphosphinate from 1-octene and sodium hypophosphite monohydrate in water/ethanol, initiated by t-butyl perbenzoate. He achieved product yields of greater than 90% by dividing the unstable initiator into two equal portions. One of them was introduced into the reaction vessel with the hypophosphite, while the second one was dissolved in the 1-octene and added gradually to the refluxing solvent system, which presumably contained preformed hypophosphite radicals. Agustin concluded that a reflux time of 45 hours was essential to obtain a product with satisfactory wetting power which was calculated to be 96% sodium octyl phosphinate. Reaction times of 12.3–15.5 hours yielded a product of low wetting power which was not further analyzed.

Attempts to prepare organic phosphinates and phosphonate esters by photochemical initiation have also resulted in low yields. A. R. Stiles et al. (U.S. Pat. No. 2,724,718) disclosed that a 54.5% yield of dibutyl octane-1-phosphonate was obtained by irradiating a mixture of 1-octene, dibutylphosphite and acetone with ultraviolet light for 7 hours at 25° C.

Due to increasing labor and energy costs, a need exists for a synthesis of alkyl phosphinates which will produce equivalent or higher yields while permitting substantially decreased reaction times.

BRIEF DESCRIPTION OF THE INVENTION

We have found that the photoinitiated reaction of an olefinic material with a hypophosphite salt to yield a phosphinate salt can be accomplished in high yields by a process comprising simultaneously adding the olefinic material and essentially all of the photoinitiator to a solution of the hypophosphite salt. In preferred embodiments of the present invention, an alcohol solution of olefinic compound and the photoinitiator are added to the hypophosphite and an aqueous alcoholic reaction medium. During the addition, the hypophosphite solution is irradiated with a source of ultraviolet light (UV).

After the addition is completed, the reaction mixture is irradiated and heated for a period of time sufficient to complete the reaction. Surprisingly, we have found that under these conditions, high yields of mono (alkyl) phosphinate salts and bis(alkyl) phosphinate salts can be obtained in higher yields than heretofore reported employing photoinitiation. For example, alpha-olefins can be reacted with sodium hypophosphite in the presence of organic peroxides in aqueous alcohol to yield sodium alkyl phosphinates and/or sodium bis(alkyl) phosphinates [$R_2P(O)ONa$] in yields of greater than 90% employing total reaction times of about 2.5–8 hours.

It was also surprisingly discovered that alkyl phosphinates prepared according to the present invention strongly complex alkaline earth metal ions, i.e. calcium ion, and are more effective sequestering agents than alkyl phosphonates. This result indicates that water-soluble n-alkyl phosphinates will be effective as builders and conditioners in detergent formulations, where they will function as substitutes or replacements for commonly-used sequestering agents such as citrates, hydroxy malonates, nitrilotriacetates and the like. These sequestering agents act to prevent or inhibit metal cations responsible for water hardness such as $Ca^{++}$ or $Mg^{++}$ from precipitating commonly used alkali metal builder salts and anionic surfactants.

DETAILED DESCRIPTION OF THE INVENTION

According to the method of the present invention, the olefinic starting material and an organic compound effective to photoinitiate the addition reaction are simultaneously added to the hypophosphite solution. The hypophosphite solution is irradiated with ultraviolet light during the addition step. Essentially all of the photoinitiator is added to the hypophosphite solution along with the olefinic component. As used herein, the term "essentially all" when used with respect to the photoinitiator, is intended to mean that substantially all of the reaction to produce the desired product is induced by the photoinitiator which is added with the olefin, e.g., that none of the photoinitiator is added to the hypophosphite solution prior to introduction of the olefinic component. While not intending to be bound by any particular theory, it is believed that the effectiveness of the present process is at least partly due to the fact that free radicals such as the $P(O)(H)ONa$ radical are produced under controlled conditions, in the presence of limited amounts of the olefinic component. Detrimental excesses of olefin are thus avoided, as sufficient free radicals are continuously present, and act immediately to convert the olefin into the phosphinate product.

The Olefinic Material

The method of the invention can be used to convert a wide variety of olefinic material into the corresponding phosphinate salts. Such olefinic materials include terminal and internal aliphatic olefins, cycloalkenes, and alpha, beta-unsaturated materials such as alpha, beta-unsaturated ketones, esters and carboxylic acids. The method of the present invention is particularly useful to form n-alkyl phosphinate salts from terminal or alpha-olefins. These olefins can have from 4–30 carbon atoms in the alkyl chain. Preferably they will have 6–20 carbon atoms in the chain. Alpha-olefins that have about 4 to 9 carbon atoms, ($C_4$–$C_9$-n-alkenes), are especially preferred substrates for use in the present method since the resulting n-alkyl phosphinates are water soluble and thus can be used to chelate hardness ions in aqueous systems. Cycloalkenes having from about 4–12 carbon atoms in the ring are also useful olefinic substrates for the present method. Also useful are olefinic materials in which the double bond is adjacent to a reactive functionality such as a ketone or one or more carboxylic acids or esters. For example, the double bond of a di-lower alkyl ester of maleic acid has been found to be reactive under the present reaction conditions. Although normally it is contemplated that the present method will be operated under conditions of ambient pressure, e.g. about one atmosphere, slight pressurization of the reaction vessels used in the present method may be necessary to prevent the loss of low boiling olefinic materials such as n-pentene, cyclobutene and the like.

The Hypophosphite Salt

Sodium hypophosphite, which is employed in the present method as its stable monohydrate, is the preferred hypophosphite salt for use in the present invention. When sodium hypophosphite is used as the hypophosphite salt, an mono(alkyl) or bis(alkyl) sodium phosphinate will be isolated as the reaction product. Although it will generally be prefered that the present method be directed toward the preparation of sodium phosphinates due to their high water solubility, stability and low cost, for some applications the preparation of other alkali metal or alkaline earth metal phosphinates may be desirable. In such cases, other alkali metal hypophosphites such as lithium hypophosphite, potassium hypophosphite, rubidium hypophosphite, cesium hypophosphite, or ammonium hypophosphite may be employed in the present reaction with the appropriate adjustment in the solvent system, reaction temperature and the like.

For the preparation of mono(alkyl) phosphinate salts, the final molar ratio of olefinic material to hypophosphite salt will fall within the range of about 1.2–0.8:1. Most preferably the molar ratio of olefinic material to hypophosphite salt will be about 1:1.

For the preparation of bis(alkyl) phosphinate salts, the final molar ratio of olefinic material to hypophosphite salt will fall within the range of about 2.5–1.5:1, most preferably about 2:1.

The Photoinitiator

In the present invention a solution of the hypophosphite salt is treated with the olefinic component and irradiated with ultraviolet light in the presence of an amount of a photoinitiator effective to initiate the free radical reaction between the hypophosphite anion and the olefinic double bond. For example, organic photoinitiators which contain aldehyde or ketone moieties which are readily converted to the excited diradical (.O—C.) state by ultraviolet radiation are useful in the practice of the presence invention. Such compounds include aldehydes such as benzaldehyde, and ketones such as acetone, methyl ethyl ketone, acetophenone, benzophenone and the like.

The amount of any photoinitiator required to catalyze the olefin-hypophosphite reaction will vary depending upon the molecular weight of the initiator and the extent of its conversion into the excited state. In the case of ketones, mole ratios of olefin to the ketone photoinitiator of 5 to 1 or more have been found to provide acceptable reaction rates.

The Solvent System

In the practice of the present invention, a solution of hypophosphite is irradiated while the olefinic component and the photoinitiator are simultaneously added into the reaction vessel containing the hypophosphite solution. Preferably the hypophosphite solution will be maintained at about 40°–80° C., preferably at about 45°–60° C. during the course of the addition and subsequent reaction period. Relatively constant temperatures within these ranges can be established by means of a refluxing azeotropic organic solvent system. The most commonly employed azeotropic solvent systems for use in the present invention are mixtures of alkanols and water. For example, mixtures of ethanol and water within the range of about 2–8 parts ethanol to each part of water can be compounded so as to reflux at temperatures of about 70°–80° C. A mixture of about 300 grams of reagent alcohol (a mixture of 95% denatured ethanol with 5% isopropyl alcohol) and 100 ml of water will reflux at a temperature of about 78° C. Other organic alcohol-water systems may be selected which will reflux within the range of about 40°–80° C. Other alcohols useful as the organic component of the present solvent systems include methanol, isopropanol, t-butanol and the like.

Reaction Methodology

In the practice of the present invention the hypophosphite salt is first dissolved in the organic solvent system in a suitable reaction vessel, and the solution brought to the desired temperature e.g. by warming the reaction vessel via water circulating in an external jacket. The olefinic material and the photoinitiator are then slowly and simultaneously added to the heated, stirred hypophosphite solution while the contents of the reaction vessel are exposed to ultraviolet light generated by an appropriate source, such as a medium pressure, quartz mercury vapor lamp. The olefinic component and the photoinitiator compound can be added neat or can be dissolved in an organic solvent which is the same as or is compatible with that used to dissolve the hypophosphite salt. Most preferably the olefinic compound and the photoinitiator will be added to the hypophosphite solution in the dropwise fashion after having been admixed, or codissolved in the same solvent. However, separate streams of the olefinic compound and the photoinitiator may be introduced into the hypophosphite solution so long as the introduction is substantially simultaneous. Once the organic compound and the photoinitiator have been introduced into the heated hypophosphite solution, irradiation is continued and the temperature of the reaction medium, the combined solutions, is maintained at or about the pre-selected temperature for a period of time effective to complete the reaction. For example, when acetone is employed in the photoinitiation of the reaction of a terminal olefin, unsaturated ester or cycloalkene with sodium hypophosphite, the typical total reaction time will be within the range of about 2.5 to 8 hours, preferably about 3 to 6 hours. At the end of this reaction time the phosphinate salt can be isolated simply by evaporating the solvents and drying the resulting solid salt in vacuo. The extent of reaction between the hypophosphite and the olefinic material to form the phosphinate is easily determinable by $^{31}P$ NMR. Mixtures of mono(alkyl) phosphinates and bis(alkyl) phosphinates can be separated by chromatographic methods well known in the art. The use of the preferred reaction times in the present method typically provides yields of phosphinate salts on the order of 80 to 100%. These yields are attained at reaction times which are substantially less than those taught to be optimal by Agustin when a thermally decomposed free radical initiator is employed.

The present invention will be further illustrated by reference to the following detailed examples.

EXAMPLE ONE

A mixture of 79.7 g Gulfteen 8 (0.71 moles, 96% 1-octene) and 8.0 g of acetone was added dropwise over a period of 3.0 hours to a 50° C. solution containing 75.5 g of sodium hypophosphite monohydrate (0.71 moles), 125.0 g of distilled water and 375 g denatured ethanol, 5% isopropyl alcohol). The reaction mixture was irradiated during the addition by a source of ultraviolet light (450 watts medium pressure, quartz, mercury-vapor lamp). Following completion of the addition, the reaction mixture was maintained at 50° C. and irradiated for an additional 2.0 hours. The resulting reaction mixture was evaporated in vacuo to yield 92% yield of sodium octyl phosphinate.

EXAMPLE TWO

A mixture of 102.3 g of dimethyl maleate (0.71 moles) and 8.0 g of acetone was added dropwise over one hour to a 50° C. solution of 75.5 g sodium hypophosphite monohydrate (0.71 moles), 125 g of distilled water and 375 g reagent alcohol. The reaction mixture was irradiated with ultraviolet light during the addition. Following completion of the addition, the reaction mixture was maintained at 50° C. and irradiated for an additional 2.5 hours. The white precipitate which formed was isolated by filtration and the filtrate evaporate in vacuo to afford 89% of sodium 2-phosphino-succinic acid dimethyl ester.

EXAMPLE THREE

A solution of 144.1 g of dimethyl maleate (1.0 moles) and 8.0 g of acetone in 400 g of a 1:1 mixture of reagent alcohol: distilled water was added dropwise over three hours to a 50° C. solution of 53.0 g of sodium hypophosphite monohydrate (0.5 mole) in 100 g reagent alcohol and 300 g distilled water. The reaction mixture was UV-irradiated during the addition and for an additional 4.0 hours at 55° C. The reaction mixture was evaporated in vacuo to afford a mixture of sodium phosphino bis(succinic acid dimethyl ester) and sodium phosphino-succinic acid dimethyl ester in greater than 97% yield.

EXAMPLE FOUR

A solution of 172.2 g diethyl maleate (1.0 mole) and 8.0 g acetone in 400 g of a 1:1 mixture of reagent alcohol: distilled water was added dropwise over 3 hours to a 50° C., UV-irradiated solution of 53.0 g sodium hypophosphite monohydrate (0.5 moles) in 100 g of reagent alcohol and 300 g distilled water. The reaction mixture was maintained at 55° C. and irradiated for an additional 4.0 hours. The reaction mixture was evaporated in vacuo to yield sodium phosphino bis(succinic acid diethyl ester) and sodium phosphino-succinic acid diethyl ester in greater than 97% yield.

It is expected that alkyl phosphinate salts prepared according to the method of the present invention will be highly effective to complex hardness factors such as calcium and magnesium cations. Thus it is expected that alkyl phosphinates which are water soluble, e.g. those containing less than about ten carbon atoms in the alkyl moietey, will be useful as builders in commercial and consumer detergent products. When used in such formulations, the present alkali metal phosphinate salts will act to inhibit or prevent the precipitation of inorganic and organic detergent components including builders such as sodium carbonate, sodium tripolyphosphate, sodium bicarbonate, sodium silicate, and the synthetic or natural alkali metal soap or nonsoap detergents.

Although the present invention has been described by reference to certain preferred embodiments, those of skill in the art will recognize that many modifications may be made therein without departing from the spirit and scope of the invention.

What is claimed is:

1. A method for the preparation of a mono(alkyl) phosphinate salt or a bis(alkyl) phosphinate salt by the reaction of an olefinic material with an alkali metal hypophosphite in the presence of a photoinitiator comprising:
   (a) simultaneously adding the olefinic material and essentially all of the photoinitiator to an about 40°–80° C. aqueous alcoholic solution of the hypophosphite while irradiating the hypophosphite solution with ultraviolet light, to form a reaction medium; and
   (b) irradiating the reaction medium with ultraviolet light while maintaining the reaction medium at about 40°–80° C. for a period of time effective to afford an about 80–100% yield of the phosphinate salt.

2. The method of claim 1 wherein the organic photosensitizer is an ketone.

3. The method of claim 1 wherein an alcoholic solution of the olefinic material and the photoinitiator is added to the hypophosphite solution.

4. The method of claim 3 wherein the hypophosphite solution and the alcoholic solution added thereto comprise ethanol.

5. The method of claim 1 wherein the olefin is an alpha-olefin and the hypophosphite is sodium hypophosphite monohydrate.

6. The method of claim 1 wherein the olefinic material is a $C_6$–$C_{22}$-alpha-olefin or a $C_5$–$C_8$-cycloalkene.

7. The method of claim 1 wherein the olefin is an olefinic dicarboxylic acid or ester.

8. The method of claim 1 wherein the mole ratio of the olefinic material to the hypophosphite is about 1:1, and the product of step (b) is an mono(alkyl) phosphinate salt.

9. The method of claim 1 wherein the mole ratio of the olefinic material to the hypophosphite is about 2:1 and the product of step (b) is a bis(alkyl) phosphinate salt.

* * * * *